(12) United States Patent
Connett-Porceddu et al.

(10) Patent No.: US 6,964,870 B2
(45) Date of Patent: Nov. 15, 2005

(54) ENHANCED SELECTION OF GENETICALLY MODIFIED PINE EMBRYOGENIC TISSUE

(75) Inventors: Marie B. Connett-Porceddu, Summerville, SC (US); Jon E. Gulledge, Goose Creek, SC (US)

(73) Assignee: MeadWestvaco Corporation, Stamford, CT (US)

( * ) Notice: Subject to any disclaimer, the term of this patent is extended or adjusted under 35 U.S.C. 154(b) by 0 days.

(21) Appl. No.: 09/973,089

(22) Filed: Oct. 10, 2001

(65) Prior Publication Data

US 2002/0083495 A1 Jun. 27, 2002

Related U.S. Application Data

(60) Provisional application No. 60/297,267, filed on Jun. 12, 2001, and provisional application No. 60/239,143, filed on Oct. 10, 2000.

(51) Int. Cl.$^7$ .............................. C12N 15/82; A01H 4/00
(52) U.S. Cl. ...................... 435/430; 435/422; 435/410; 800/268; 800/294
(58) Field of Search .................................. 435/430, 422, 435/410, 469, 430.1; 800/268, 294, 319

(56) References Cited

U.S. PATENT DOCUMENTS

| | | | |
|---|---|---|---|
| 5,187,092 A | | 2/1993 | Uddin |
| 5,731,204 A | * | 3/1998 | Rutter et al. ................ 435/430 |
| 5,952,486 A | | 9/1999 | Bloksberg et al. |
| 6,200,809 B1 | | 3/2001 | Klimaszewska et al. |
| 6,340,594 B1 | | 1/2002 | Attree et al. |

OTHER PUBLICATIONS

Wenck et al., High–efficiency Agrobacterium–mediated transformation of Norway . . . , 1999, Plant Molecular Biology, vol. 39, pp. 407–416.*

Levee et al., Stable gentic transformation of white pine ( *Pinus strobus* L. ) after covultivation of embryogenic tissuses with *Abgrobacterium tumefaciens*, 1999, Molecular Breeding, vol. 5, pp. 429–440.*

Wenck et al (1999, Plant Molecular Biology 39(3):407–416).*

Levee et al (1999, Molecular Breeding 5:429–440).*

Pending U.S. Appl. Ser. No. 09/973,369, filed Oct. 9, 2001.

Kong, Y. et al. (1988). "Culture of asparagus protoplasts on porous polypropylene membrane," *Plant Cell Reports* 7:67–69.

A.R. Wenck et al., "High–efficiency *Agrobacterium*–mediated transformation of Norway spruce (*Picea abies*) and loblolly pine (*Pinus taeda*)," Plant Molecular Biology 39:407–416, 1999.

T. Wei et al., "Studies on embyogenic callus induction and plant regeneration in Loblolly Pine," Scientia Silvae Sinicae 34(3):115–119, May 1998, English Abstract.

T. Wei et al., "Preliminary Studies on Establishment of Genetic Transformation System in Loblolly Pine," Journal of Forestry Research 8(4):201–205, Dec. 1997.

* cited by examiner

*Primary Examiner*—Elizabeth McElwain
*Assistant Examiner*—Stuart F. Baum
(74) *Attorney, Agent, or Firm*—Rothwell Figg Ernst & Manbeck

(57) ABSTRACT

The present invention relates to methods for the selection of transformed embryogenic tissue of coniferous plants. In particular, the invention relates to improved methods for selecting transformed embryogenic tissue of plants of the subgenus *Pinus* of pines, particularly Southern yellow pines and hybrids thereof using an agent that regulates differentiation of embryos from embryogenic cells.

19 Claims, No Drawings

ENHANCED SELECTION OF GENETICALLY MODIFIED PINE EMBRYOGENIC TISSUE

The present application is related to U.S. provisional patent application Ser. No. 60/297,267 filed on Jun. 12, 2001 and to U.S. provisional patent application Ser. No. 60/239,143 filed on Oct. 10, 2000, each incorporated herein by reference, and priority thereto is claimed under 35 USC §119(e).

BACKGROUND OF THE INVENTION

The present invention relates to methods for the transformation and regeneration of transformed embryogenic tissue of coniferous plants. In particular, the invention relates to improved methods for transforming embryogenic tissue of coniferous plants and for regenerating transformed embryogenic tissue of coniferous plants. The invention is well suited to the transformation and regeneration of transformed embryogenic tissue of plants of the subgenus *Pinus* of pines.

The publications and other materials used herein to illuminate the background of the invention or provide additional details respecting the practice, are incorporated by reference, and for convenience are respectively grouped in the appended Bibliography.

Reforestation, the controlled regeneration of forests, has become an integral part of forest management in order to secure a renewable and sustainable source of raw material for production of paper and other wood-related products. Forest trees can be regenerated by either sexual or asexual propagation. Sexual reproduction of seedlings for reforestation has traditionally been the most important means of propagation, especially with coniferous species.

Tree improvement programs with economically important conifers (e.g., *Pinus, Picea,* and *Pseudotsuga* species) have applied genetic principles of selection and breeding to achieve genetic gain. Based on the results of progeny tests, superior maternal trees are selected and used in "seed orchards" for mass production of genetically improved seed. The genetic gain in such an open-pollinated sexual propagation strategy is, however, limited by the breeder's inability to control the paternal parent. Further gains can be achieved by control-pollination of the maternal tree with pollen from individual trees whose progeny have also demonstrated superior growth characteristics. Yet sexual propagation results in a "family" of seeds comprised of many different genetic combinations (known as siblings), even though both parents of each sibling seed are the same. As not all genotype combinations are favorable, the potential genetic gain is reduced due to this genetic variation among sibling seeds.

In addition to these genetic limitations, large-scale production of control pollinated seeds is expensive. These economic and biological limitations on large-scale seed production have caused considerable interest to develop in the industry for applying asexual methods to propagate economically important conifers.

The use of asexual propagation permits one to apply what is known as a very high selection intensity (that is, to propagate only progeny showing a very high genetic gain potential). These highly desirable progeny have unique genetic combinations that result in superior growth and performance characteristics. Thus, with asexual propagation it is possible to multiply genetically select individuals while avoiding a concomitant reduction of genetic gain due to within-family variation. Asexual propagation of trees can be accomplished by methods of grafting, vegetative propagation, and micropropagation. Micropropagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Both vegetative propagation and micropropagation have the potential to capture all genetic gain of highly desirable genotypes. However, unlike conventional vegetative propagation methods, somatic embryogenesis is amenable to automation and mechanization, making it highly desirable for large-scale production of planting stock for reforestation. In addition, somatic embryogenic cultures can easily be preserved in liquid nitrogen. Having a long-term cryogenic preservation system offers immense advantages over other vegetative propagation systems which attempt to maintain the juvenility of stock plants.

One source of new genetic material for use in reforestation or tree improvement programs is plant tissue that has been transformed to contain one or more genes of interest. Genetic modification techniques enable one to insert exogenous nucleotide sequences into an organism's genome. A number of methods have been described for the genetic modification of plants, including transformation via biolistics and *Agrobacterium tumefaciens*. All of these methods are based on introducing a foreign DNA into the plant cell, isolation of those cells containing the foreign DNA integrated into the genome, followed by subsequent regeneration of a whole plant.

A significant problem in production of transgenic plants is how to recover only transformed cells following transformation, while causing minimal perturbations to their health so that they can proliferate, give rise to differentiating cultures and ultimately regenerate transgenic plants.

It is well known that embryogenic cultures, in general, and pine embryogenic cultures, specifically, can experience significant decline in regeneration potential under stressful culture conditions. Stresses to the cells during and after transformation can include the perturbations of the transformation process (which may include co-cultivation with *Agrobacteria,* bombardment with microprojectiles, chemical treatments, electroporation or mechanical shearing), any measures that allow preferential growth of transformed cells while selectively killing or depressing the growth or regeneration of untransformed cells (referred to as "selection"), exudates released from dying cells in the culture, and/or the elicitation of transgene activity in the transformed cells (for "positive selection" or detection of the activity of "visual marker genes"). It stands to reason that when transformed cells are not maintained in sufficient health to allow their survival through these stresses, not only will they fail to give rise to transgenic plants, they may never be detected as transformed in the first place.

Regeneration of transformed plants from transformed cultures of pine has been difficult. Reports of pine transformation and regeneration include the following:

U.S. Pat. No. 4,459,355 (Cello and Olsen, 1984) describes a method for using *Agrobacterium tumefaciens* to transform plant cells. The patent claims transformation of any dicotyledon or any gymnosperm (e.g. loblolly pine, cedar, Douglas fir). However, no example of transformation of any gymnosperm is given. Thus, a claim of stable transformation of pines following inoculation with *Agrobacterium tumefaciens* was allowed in U.S. Pat. No. 4,886,937 (Sederoff et al., 1989).

U.S. Pat. No. 4,886,937 also claims the transformed pine obtained from inoculation with *Agrobacterium tumefaciens*.

However, no transformed pine plants were obtained in the examples, which are restricted to formation of non-regenerable galls following inoculation of seedlings. Further work by researchers in the same lab, using *Agrobacterium tumefaciens* to inoculate pine and spruce somatic embryogenic cultures, was published (Wenck et al., 1999). In the work described in that publication, stable transformation of both species was achieved, but while plants were regenerated from the transformed spruce cultures, no plants could be obtained from the loblolly pine cultures.

In particle-mediated gene transfer, the DNA of interest is precipitated onto the surface of carrier particles which are subsequently accelerated toward a piece of target tissue. The carrier particles penetrate the cell wall of the plant cell, wherein the DNA can be expressed, and may integrate with the chromosomal DNA. In some instances stable expression results if the transforming DNA integrates with the chromosomal DNA (Walter et al. 1994), but sorbitol pre-treatments described as important for obtaining stable expression were not taught for regeneration of transformed pine plants (Walter et al. 1997), perhaps because, as we found, such treatments can also be detrimental to the regeneration of pine plants. To obtain high frequency gene transfer and regeneration of plants in the genus *Pinus*, we developed a variety of high gelling agent or high osmoticum preparation media for use before transformation and selection in pines, described in U.S. patent application Ser. No. 09/318,136 filed on 25 May 1999 and New Zealand Patent No. 336149, each incorporated herein by reference.

Although regeneration of planting stock of transformed pine via biolistic processes has been reported as described above, transformed sublines and transformed plants had never been detected or recovered from pine embryogenic lines of certain genetic backgrounds. One problem has been that embryogenic masses from many species of pines cannot be maintained for long periods on media before culture decline is observed in many lines. For example, culture decline is observed to occur frequently with progeny of the *P. taeda* elite selection 7–56, an unfortunate circumstance because these crosses are considered genetically valuable and are used in many breeding programs. Although such material would be a desirable substrate for transformation, any delay in embryo formation, which can be caused for example by the sometimes lengthy period of selection following transformation, and the period of bacterial eradication following particularly *Agrobacterium* transformation, exacerbates the problem of culture decline.

A measure taken to speed up selection and increase proliferative health followed the observation that abscisic acid (ABA) in the gelled media is important in order to obtain transformed embryogenic masses from certain embryogenic lines, while it does not prevent growth of stably transformed embryogenic masses of many other pine genotypes, including interspecific hybrids. In other words, the addition of ABA to the media used for transformation and post-transformation recovery and growth is either neutral, or beneficial for certain genotypes. Because maintenance, recovery and selection media containing ABA support as good or better growth rates as media lacking ABA, selection of transformed lines is accomplished more rapidly, increasing the health of the cells going into the embryo development phase and decreasing the time prior to differentiation of embryos. Thus, regeneration of transformed plants is enhanced as a result of increased proliferative health of transformed tissue by the inclusion of ABA in the culture media. It has also been found that the presence of ABA in the preparation media for transformation, i.e., the preparation media used for bombardment or co-cultivation with *Agrobacterium*, can in some genotypes assist transformed cells to survive the stress of transformation.

The importance of abscisic acid (ABA) during the development and maturation of zygotic embryos is well known, and ABA has been used routinely to stimulate terminal embryo development in somatic embryogenic systems (von Arnold and Hakman, 1988). For example, U.S. Pat. No. 4,957,866 teaches the use of ABA in the terminal embryo development media. Likewise, in U.S. Pat. Nos. 5,034,326 and 5,036,007 the phytohormone ABA along with activated carbon has been reported to be beneficial in gelled embryo development media for various conifers. U.S. Pat. No. 5,294,549 teaches the incorporation of ABA and gibberellic acid into the embryo development media. U.S. Pat. Nos. 5,187,092, 5,183,757, and 5,236,841 teach the use of ABA in the terminal embryo development step in conifer somatic embryogenesis. In each of these methods ABA is added for the purpose of facilitating terminal embryo development to the cotyledonary stage for the regeneration of plants.

Terminal development of embryos for the regeneration of plants from somatic embryogenic tissue is effected not only by the addition of ABA but also by affecting the water potential of the embryogenic tissue, either by the use of polyethylene glycol or other osmotica (see for example U.S. Pat. No. 5,036,007) or by separating the somatic embryos from a liquid medium by a porous support, or by introducing a gelling agent (e.g. gellan gum) into the medium in larger than normal quantities (see for example in U.S. Pat. No. 6,200,809) for the purposes of obtaining terminal embryo development.

Heretofore there has been no evidence that the use of ABA or manipulation of the water potential during selection, either in plants in general or with coniferous species, would be beneficial. In fact, although it is well known that these factors are important in the terminal development of embryos both in vivo and in vitro, their ability to stimulate recovery of transformed embryogenic tissue so that proliferative growth can resume in transformed cells of elite lines of *P. taeda* and hybrids was unexpected.

The developmental stage of the explant tissue used to initiate embryogenic cultures in conifers is critically important. Pines have proven much more restricted than spruces in terms of the responsive embryo development stage for somatic embryogenic culture initiation. To be successful in pines, one must use only very immature embryos (or seeds containing such immature embryos). The size of the developing embryo, usually measured as length, has frequently been used to determine the appropriate developmental stage for culture initiation in many plant species. This has been the case with loblolly pine where it was found that the embryogenic culture initiation occurred most frequently when the dominant zygotic embryo was less than about 0.5 mm in length.

Because it is difficult to measure the size of very immature differentiated embryos, embryo staging systems have also been used to make the determination of the appropriate developmental stage easier. These staging systems are based on several factors, including various morphological characteristics of the embryo. An embryo staging system proposed by Hakman and von Arnold (1988), which is commonly utilized in the industry, has the following three distinct stages. Stage 1 embryos are small differentiated embryos consisting of an embryonic region of small, densely cytoplasmic region subtended by a suspensor comprised of long, highly vacuolated cells. Stage 2 embryos are further differentiated embryos with a prominent embryonic region that becomes more opaque and assumes a smooth and glossy surface. Stage 3 embryos are further differentiated embryos which show visible cotyledonary primordia. Thus, stage 1 and 2 embryos are at a pre-cotyledonary stage of development, while stage 3 embryos are cotyledonary. As used herein, the term "pre-stage 3 embryo" means a differentiated pre-cotyledonary embryo (i.e., a stage 1 or stage 2 embryo). Although the above three-stage system was first used with somatic embryos of spruce, it is generally applicable to both somatic and zygotic embryos of all conifer species.

As described in U.S. patent application Ser. No. 09/318,136 filed on 25 May 1999 and New Zealand Patent No. 336149, each incorporated herein by reference, it has been observed that the presence in the tissue of embryos at the proper precotyledonary stage was both necessary and sufficient for efficient transformation of the genus Pinus. Differentiation of tissue to the appropriate stage of embryo development was aided by manipulation of osmoticum and gelling agent concentrations to obtain matrix potentials sufficient to prepare the tissue for transformation. It was further observed that transfer of precotyledonary embryos to a maintenance medium, with or without a selection agent, allowed cells on the embryos to re-initiate secondary somatic embryogenesis, and the embryogenic tissue so derived is then able to resume proliferative growth. Following transformation, selection of such embryogenic tissue is needed in order to generate transgenic embryogenic cell lines.

It had previously been found that both ABA and manipulation of gelling agent concentrations can contribute to more efficient culture initiation in pine. U.S. Pat. No. 5,506,136 by Becwar et al. (1996) describes the use of a reduced gelling agent concentration to obtain higher frequency of initiation. U.S. Pat. No. 5,856,191 by Handley (1999) employs ABA as an improvement upon the methods described in U.S. Pat. No. 5,506,136 in both the initiation and maintenance medium for pine embryogenic cultures prior to cryopreservation. The utility of ABA in obtaining improved conditions for culture initiation was unexpected, as in this case.

In U.S. Pat. No. 5,856,191, the use of ABA is coupled with another method that is known to regulate conifer embryo development, namely manipulation of the matrix potential of the gelled medium.

Accordingly, we investigated whether the addition of ABA or the manipulation of the matrix potential of the gelled medium might be able to stimulate recovery of transgenic cell lines from selection, in a mode of action similar to the stimulation that these agents are able to provide, separately or together, in initiation of primary somatic embryogenesis in the genus Pinus.

Thus, it is an object of the present invention to provide an improved method for the selection of transformed embryogenic cultures and regeneration of transformed coniferous plants.

SUMMARY OF THE INVENTION

The present invention relates to methods for the selection of transformed embryogenic cultures and the regeneration of transformed embryogenic tissue of coniferous plants. The invention is well suited to the transformation and regeneration of transformed embryogenic tissue of plants of the subgenus Pinus of pines, particularly the Southern yellow pines and hybrids thereof. The present invention provides for the first time the regeneration of plants suitable for field planting from lines of certain elite genetic backgrounds of Southern yellow pines.

Selection is improved and the subsequent proliferation of transformed tissue is increased by using an agent that regulates differentiation of embryos from embryogenic cells. Suitable agents include abscisic acid (ABA), an osmoticum and a gelling agent, or combinations thereof. A non-limiting example of an osmoticum is polyethylene glycol (PEG). A non-limiting example of a gelling agent is gellan gum. The gelling agent is used at concentration which is either higher than that normally used in plant tissue culture media or lower than that normally used in plant tissue culture media.

In one embodiment of the present invention, selection is improved and the subsequent proliferation of transformed tissue is increased by using ABA in one or more of the transformation, recovery and selection media. We hypothesized that ABA may be involved in the switch between proliferation and differentiation, facilitating the development of precotyledonary embryos and initiation of secondary somatic embryogenesis on them, but preventing use of the nutrients in the media for precocious further differentiation to terminal embryo development, and favoring redirection toward proliferation as a result. We further hypothesized that cells in a proliferative mode would be more able to withstand and recover from certain types of stresses that might be lethal to differentiating embryos, because secondary somatic embryogenesis and subsequent proliferation can occur from smaller and less intact cell masses than can terminal differentiation into embryos (differentiating cells normally lose their totipotency). This model predicts that cells maintained in a secondary embryogenesis mode by ABA should be better able to withstand and recover from the stresses of transformation. In line with our prediction, we were able to detect for the first time, solely in treatments containing ABA in the selection media, confirmed proliferating transformant sublines from lines that normally show the precocious development and early decline characteristics.

It has been observed that in a large number of experiments, using both Agrobacterium and bombardment transformation methods, that ABA is important in order to obtain transformed embryogenic masses from certain embryogenic lines. For example, many more transformants (more than 80% of the lines attempted) have been recovered from the cross 7-56×9-6, a cross in which culture decline is frequently seen and transformed tissue had not been recovered. These transformed lines are always being found solely in treatments that utilized ABA in the selection media. Stable transformants were detected after nine weeks of selection in a treatment in which ABA had been added to the medium only during the first week of selection, and progressively more transformants were detected in treatments in which ABA was added to the selection medium during the first three or six weeks or throughout the entire nine-week selection period. This result implies that the protective effect of the ABA which allows transformed cells to survive selection is already being exerted in the initial period of selection, but that it is beneficial throughout the selection period and that without it transformants are being lost before they can be detected. This result demonstrated that the previous failure to detect stable transformants from the cross 7-56×9-6 did not result from failure to transform any cells, but from failure of these transformed pine cells to grow during selection without ABA. These effects have been observed on media containing 5–30 mM ABA.

It has also been observed that the addition of ABA to the selection media does not prevent detection of stably transformed embryogenic masses of many other pine genotypes, including interspecific hybrids. It has further been observed that addition of ABA to the recovery media (the media onto which cells are transferred following transformation, before they are subjected to selective growth or positive selection) did not significantly increase the number of transformants detected, but did not decrease it either, and may have supported the recovering health of the cells going into selection. For example, it has been observed that in certain lines or hybrids, pine somatic embryogenic masses cultured in the presence of ABA after being subjected to co-cultivation with *Agrobacterium* were able to double more rapidly than pine somatic embryogenic masses which were cultured after co-cultivation in a recovery medium that did not contain ABA. In other words, the addition of ABA to the media used for transformation and post-transformation recovery and growth is either neutral, or beneficial (required for certain genotypes).

Finally, it has been observed that ABA may assist transformed cells to survive when it is added to the preparation media used for bombardment or co-cultivation. For example, pine somatic embryogenic masses of all lines cultured in the presence of 10 to 30 mg/L ABA during and after co-cultivation with *Agrobacterium* showed fewer necrotic foci (these appeared upon microscopic examination to be derived from the death of precociously developing embryos in the cultures) than did pine somatic embryogenic masses which were cultured during and after co-cultivation on media that did not contain ABA. In addition, a surprisingly high frequency of transformants from several lines of the cross 7-56×9-6 and other lines, including some interspecific hybrids, was detected in experiments in which a preparation medium for bombardment contained a high level of ABA (125 mg/L) was used for bombarding precotyledonary embryos.

Because recovery and selection media containing ABA support as good or better growth rates as media lacking ABA, we are able to accomplish selection of transformed lines more rapidly, increasing the health of the cells going into the embryo development phase and decreasing the time prior to differentiation of embryos. Thus, in accordance with the present invention, it is now a standard practice to include 5–30 mM ABA in the gelled media used following transformation. It is also preferred to use ABA in the transformation media, i.e., the preparation media for bombardment or the co-cultivation media for *Agrobacterium*.

In a second embodiment of the present invention, it has also been observed that similar effects can be obtained by manipulation of the matrix potential of the selection medium. For lines in which we observe either precocious or delayed embryo development on maintenance medium, it is preferred to lower or raise, respectively, the concentration of gelling agent in order to obtain precotyledonary embryos at the appropriate stage for continued secondary embryogenesis and subsequent proliferative growth of embryogenic cell lines. In the absence of such a manipulation either by the administration of ABA or the alteration of the matrix potential during selection, such lines tend to show fewer or no healthy proliferating embryogenic transformed sublines following transformation and selection.

Accordingly, it has been found that the coupling of the ABA concentrations and/or gelling agent manipulations taught for initiation of primary somatic embryogenesis in U.S. Pat. No. 5,856,191, with the method for biolistic transformation and selection, described in U.S. pat. application Ser. No. 09/318,136 filed on 25 May 1999 and New Zealand Pat. No. 336149, each incorporated herein by reference, or with the method for *Agrobacterium* transformation and selection, described in U.S. pat. application Ser. No. 09/973,088 filed concurrently herewith, entitled "Enhanced Transformation and Regeneration of Transformed Embryogenic Pine Tissue" incorporated herein by reference, yields a marked improvement in the growth of embryogenic cultures during the critical phase of selection.

Culture of pine embryogenic cells on media containing a lowered gelling agent concentration is facilitated by the use of highly liquid-permeable membrane supports, made from low-absorption fibers such as polyester and other non-cellulosic fibers with similar characteristics described in U.S. pat. application Ser. No. 09/973,088 filed concurrently herewith, entitled "Enhanced Transformation and Regeneration of Transformed Embryogenic Pine Tissue," incorporated herein by reference.

Selection of genetically transformed pine cells is improved by the use of this method, and selection of genetically transformed pine cells from certain lines, progeny of elite crosses, is enabled for the first time by the use of this method. With the use of these means, selection of transformed lines is accomplished more rapidly, as well as increasing the health of the cells going into the embryo development phase and decreasing the time prior to differentiation of embryos.

DETAILED DESCRIPTION

This improvement allows selection of transformed embryogenic cultures and the regeneration of transformed embryogenic tissue of coniferous plants, particularly Southern yellow pines and hybrids thereof. Examples of Southern Yellow pines include *Pinus taeda, Pinus elliotii,* and *Pinus caribaea* and related pines.

Our method to speed up selection and increase proliferative health, which is preferred for Southern yellow pines such as *P. taeda, Pinus elliotii,* and *Pinus caribaea* and related pines and hybrids thereof (although reference is made in the description which follows to *P. taeda* for convenience, it is understood to mean all Southern yellow pines), followed the observation that abscisic acid (ABA) in the gelled media is important in order to obtain transformed embryogenic masses from certain *P. taeda* embryogenic lines, while it does not prevent growth of stably transformed embryogenic masses of many other pine genotypes, including interspecific hybrids. In other words, the addition of ABA to the media used for transformation and post-transformation recovery and selective growth of transformed *P. taeda* is either neutral, or beneficial for certain genotypes. Because recovery and selection media containing ABA support as good or better growth rates of transformed *P. taeda* as media lacking ABA, selection of transformed lines is accomplished more rapidly. Decreased time on selection media increases the health of the cells going into the embryo development phase and decreases the time prior to differentiation of embryos. Thus, regeneration of transformed plants is enhanced as a result of increased proliferative health of transformed tissue by the inclusion of ABA in the selection media. It has also been found that the presence of ABA in the preparation media for transformation, i.e., the preparation media used to prepare the pine cells for bombardment or co-cultivation with *Agrobacterium,* assists transformed cells of certain *P. taeda* lines to survive the stress of transformation.

Thus, the present invention provides a method for enhancing selection of genetically modified pine embryogenic tissue. Selection is improved and the subsequent proliferation of transformed tissue is increased by using an agent that regulates differentiation of embryos from embryogenic cells. Suitable agents include abscisic acid (ABA), an osmoticum and a gelling agent or combinations thereof. A non-limiting example of an osmoticum is polyethylene glycol (PEG). A non-limiting example of a gelling agent is gellan gum. The gelling agent is used at concentration which is either higher than that normally used in plant tissue culture media or lower than that normally used in plant tissue culture media. Higher concentrations of gelling agent are preferably in the range of about 3% to about 5%. Lower concentrations of gelling agent are preferably in the range of about 0.5% to about 1.5%.

For a number of pine species including Southern yellow pines such as *P. taeda Pinus elliotii,* and *Pinus caribaea* and related pines and hybrids, selection is improved and the number of proliferating transformed cell lines recovered is increased by using ABA in one or more of the recovery and selection media. We hypothesized that concentrations of ABA of 5–90 mg/L in these media, which are based on the same nutrient composition as some initiation and proliferation media, may be involved in the switch between proliferation and differentiation, maintaining the cells at the appropriate embryogenic stage for the initiation and continuation of secondary somatic embryogenesis as a result. We further hypothesized that cells in this appropriate developmental state would be more able to withstand and recover from certain types of stresses that might be lethal to differentiating embryos, because initiation of secondary somatic embryogenesis and further proliferation can occur from smaller and less intact cell masses than can differentiation (differentiating cells normally lose their totipotency). This model predicts that cells maintained at the stage appropriate for continued re-initiation of secondary somatic embryogenesis by concentrations of ABA of 5–90 mg/L should be better able to withstand and recover from the stresses of transformation, and subsequently proliferative growth of the secondary somatic embryogenic tissue would be favored. In line with our prediction, we were able to detect for the first time, solely in treatments containing ABA in the selection media, confirmed transformants from lines that normally show the precocious development and early decline characteristics.

It has been observed that in a large number of experiments, using both *Agrobacterium* and bombardment transformation methods, that ABA is important in order to obtain transformed embryogenic masses from certain embryogenic lines. For example, many more transformants (in more than 80% of the lines attempted) have been recovered from crosses with the elite *P. taeda* selection 7–56 as a parent, in which culture decline is frequently seen and transformed tissue had not been recovered. These transformed lines are seldom found in treatments that did not utilize ABA in the selection media. In contrast, multiple stable transformants were detected after selection in a treatment in which ABA had been added to the medium only during the first week of selection, and progressively more transformants were detected in treatments in which ABA was added to the selection medium during three, six, or nine weeks of the selection period. This result implies that the protective effect of the ABA which allows transformed cells to survive selection is already being exerted in the initial period of selection, but that it is beneficial throughout the selection period and that without it transformants are being lost before they can be detected. This result demonstrated that the previous failure to detect stable transformants from a particular cross with the parent 7-56 did not result from failure to transform any cells, but from failure of these transformed pine cells to grow during selection without ABA. These effects have been observed on media containing 5–30 mg/L ABA.

It has also been observed that the addition of ABA to the selection media does not prevent detection of stably transformed embryogenic masses of many other pine genotypes, including interspecific hybrids. It has further been observed that addition of ABA to recovery media (media on which cells may be cultured following transformation, for example during eradication, before they are subjected to selective growth or positive selection) did not significantly increase the number of transformants detected, but did not decrease it either, and may have supported the recovering health of the cells going into selection. For example, it has been observed that in certain *P. taeda* lines and hybrids, pine somatic embryogenic masses cultured in the presence of ABA after being subjected to co-cultivation with *Agrobacterium* were able to double more rapidly than pine somatic embryogenic masses which were cultured after co-cultivation in a recovery medium that did not contain ABA. In other words, the addition of ABA to the media used for post-transformation recovery and growth is either neutral, or beneficial (required for certain genotypes) for Southern yellow pines and their hybrids. For certain genotypes, ABA may also be used in the transformation media.

Because recovery and selection media containing ABA support as good or better growth rates as media lacking ABA, we are able to accomplish selection of transformed lines more rapidly, increasing the health of the cells going into the embryo development phase and decreasing the time prior to differentiation of embryos. Thus, in accordance with the present invention, it is now our practice to include 5–30 mg/L ABA in the gelled media used to recover and proliferate transformed cells following transformation, i.e. recovery media, eradication media, growth media, and selection media that encourage secondary somatic embryogenesis and subsequently the healthy proliferative growth of transformed cell lines.

As described in U.S. patent application Ser. No. 09/318, 136 filed on 25 May 1999 and New Zealand Patent No. 336149, each incorporated herein by reference, it has been observed that the presence in the tissue of embryos at the proper precotyledonary stage was both necessary and sufficient for efficient transformation of the genus *Pinus*. Differentiation of tissue to the appropriate stage of embryo development was aided by manipulation of osmoticum and gelling agent concentrations to obtain matrix potentials sufficient to prepare the tissue for transformation. It was further observed that transfer of precotyledonary embryos to a maintenance medium, with or without a selection agent, allowed cells on the embryos to re-initiate secondary somatic embryogenesis, and the embryogenic tissue so derived is then able to resume proliferative growth. Following transformation, selection of such embryogenic tissue is needed in order to generate transgenic embryogenic cell lines.

For the purposes of obtaining terminal embryo development, manipulation of the developmental stage of embryos by affecting the water potential of the embryogenic tissue, either by separating the somatic embryos from a liquid medium by a porous support, or by introducing a gelling agent (e.g. gellan gum) into the growth medium in larger than normal quantities, is taught in U.S. Pat. 6,200, 809. In the present invention, we employ similar means to affect the developmental stage of the embryos during selection, not to favor terminal embryo development. As taught in U.S. Pat. Nos. 5,506,136 and 5,856,191, primary initiation of *Pinus* embryogenic cultures is favored not only by ABA in the medium at similar concentrations, but also by manipulation of the matrix potential by use of a GEL-TRITE® gelling agent concentration lower than that commonly taught in plant tissue culture, i.e. between 0.5% and 2% GELRITE® gelling agent in DCR nutrient media, wherein previous methods had used 2% GELRITE® gelling agent in media of similar salt composition, and 2% GEL-RITE® gelling agent is also commonly used in maintenance and selection media of similar salt composition. Accordingly, we hypothesized that manipulation of the matrix potential in transformation, recovery and selection media might enhance initiation of secondary somatic embryogenesis in transformed precotyledonary embryos, particularly in some lines in which precocious embryo development is observed in the absence of such manipulation.

It has indeed been observed that similar effects can be obtained by manipulation of the matrix potential of the selection medium. For lines in which we observe either precocious or delayed embryo development on maintenance medium, it is preferred to lower or raise, respectively, the concentration of gelling agent in order to obtain precotyledonary embryos at the appropriate stage for continued secondary embryogenesis and subsequent proliferative growth of embryogenic cell lines. In the absence of such a manipulation either by the administration of ABA or the alteration of the matrix potential during selection, such lines tend to show fewer or no healthy proliferating embryogenic transformed sublines following transformation and selection.

Culture of pine embryogenic cells on media containing a lowered gelling agent concentration is facilitated by the use of highly liquid-permeable membrane supports, made from low-absorption fibers such as polyester and other noncellulosic fibers with similar characteristics, in plant tissue culture processes. Such supports prevent the sinking and embedding into the low gelled medium of the embryogenic tissue maintained on the surface, while still allowing the penetration of media components through the supports into the tissue. It is preferred to use a support membrane prepared from material selected from the group consisting of polyesters, polypropylenes, liquid-permeable fluoropolymer fabrics, and combinations thereof.

Selected, healthy transformed cells are cultured using conventional techniques for somatic embryogenesis of Southern yellow pines and hybrids thereof, such as described in Becwar et al. (1990; 1995; 1996), Handley and Godbey (1996) and Handley (1999), to produce transgenic somatic embryos and to regenerate plants from the transgenic embryos, such as by germination of the somatic embryos. Transgenic plants of *Pinus* species are generated from selected healthy transformed cells in accordance with similar techniques or techniques known in the art for regenerating plants of these species.

The present invention is generally useful for improving the growth of transgenic pine cell and embryogenic cultures.

The present invention is useful for improving selection of transformed cells by exposure of pine embryogenic cultures to selection agents (e.g. antibiotics and herbicides), following the application of a genetic transformation protocol, of which many are known to those skilled in the art, including but not limited to transformation by *Agrobacterium* or biolistics.

The present invention is further useful for improving facilitating the recovery of transformed embryogenic sublines from pine embryogenic cultures subjected to transformation followed by selective growth, positive selection, or detection of transgenes.

EXAMPLES

The present invention is further described in the following examples, which are offered by way of illustration and are not intended to limit the invention in any manner. Standard techniques well known in the art or the techniques specifically described below are utilized.

Example 1

Preparation of Embryogenic Cultures,
Transformation by a BIOLISTIC® Method, and
Selection of Transformed Sublines with or without
ABA in the Selection Medium Loblolly pine (*Pinus taeda*) embryogenic cell lines were initiated from zygotic embryos of individual immature megagametophytes as previously described (Becwar et al. 1996). The procedure was as follows. Immature seed cones were collected from Westvaco's South Carolina coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

For culture initiation intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process. Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium, $DCR_1$ or $WV5_1$ initiation medium.

Basal salt mixtures which have proven effective for pine embryogenesis culture initiation include but are not limited to the DCR or WVN5 basal salts formulations listed in Table 1. Complete media formulations used in initiation, maintenance and proliferative growth of pine embryogenic cultures in this and later Examples are listed in Table 2. The pH of the medium had been adjusted to 5.8 with KOH and HCl prior to autoclaving at 110 kPa (16 psi) and 121° C. for 20 minutes, and approximately 20 ml of medium had been poured into 100×15 mm sterile plastic petri dishes. Those skilled in the art of plant tissue culture will recognize that many other formulations, sterilization conditions, and media volumes would be applicable to the use of the present method.

TABLE 1

Basal Culture Media Formulations Used For Pine Embryogenesis

| COMPONENT | WV5[a] | DCR[b] | MSG[c] |
|---|---|---|---|
| | \multicolumn{3}{c}{CONCENTRATION (mg/L)} | | |
| INORGANIC SALTS | | | |
| $NH_4NO_3$ | 700.00 | 400.00 | 0 |
| $KNO_3$ | 259.00 | 340.00 | 100.00 |
| $Ca(NO_3)_2 4H_2O$ | 963.00 | 556.00 | 0 |
| $MgSO_4 7H_2O$ | 1850.00 | 370.00 | 370.00 |
| $KH_2PO_4$ | 270.00 | 170.00 | 170.00 |
| $CaCl_2 2H_2O$ | 0 | 85.00 | 440.00 |
| KCl | 1327.00 | 0 | 745.00 |
| KI | 0.83 | 0.83 | 0.83 |
| $H_3BO_3$ | 31.00 | 6.20 | 6.20 |
| $MnSO_4 H_2O$ | 15.16 | 22.30 | 16.90 |
| $ZnSO_4 7H_2O$ | 8.60 | 8.60 | 8.60 |
| $Na_2MoO_4 2H_2O$ | 0.25 | 0.25 | 0.25 |
| $CuSO_4 5H_2O$ | 0.25 | 0.25 | 0.03 |
| $CoCl_2 6H_2O$ | 0.03 | 0.03 | 0.03 |
| $NiCl_2 6H_2O$ | 0 | 0.03 | 0 |
| $FeSO_4 7H_2O$ | 27.80 | 27.80 | 27.80 |
| $Na_2EDTA$ | 37.30 | 37.30 | 37.30 |
| VITAMINS, AMINO ACIDS | | | |
| Nicotinic acid | 0.50 | 0.50 | 0.50 |
| Pyridoxine HCl | 0.50 | 0.50 | 0.10 |
| Thiamine HCl | 1.00 | 1.00 | 0.10 |
| Glycine | 2.00 | 2.00 | 0 |
| Glutamine[d] | 0 | 250.00 | 1450.00 |

[a]According to Coke (1996).
[b]According to Gupta and Durzan (1985).
[c]According to Becwar et al. (1990).
[d]Added as a filter-sterilized aqueous stock to autoclaved medium while still warm (about 60° C.).

TABLE 2

Initiation, Maintenance, And Proliferation Media Formulations Used For Pine Embryogenesis

| COMPONENT | Gelled Initiation Medium $WV5_1$ | Gelled Initiation Medium $DCR_1$ | Gelled Maintenance Medium $WV5_2$ | Gelled Maintenance Medium $DCR_2$ | Preparation Medium $DCR_3$ | Liquid[f] Proliferation Medium $DCR_4$ |
|---|---|---|---|---|---|---|
| Basal medium[a] | WV5 | DCR | WV5 | DCR | DCR | DCR |
| | \multicolumn{6}{c}{Concentration (g/L)} | | | | | |
| Inositol | 0.50 | 0.50 | 0.50 | 0.50 | 0.50 | 0.50 |
| Casein hydrolysate[b] | 0.50 | 0.50 | 0.50 | 0.50 | 0.50 | 0.50 |
| L-glutamine | 0 | 0.25 | 0 | 0.25 | 0.25 | 0.25 |
| Sucrose | 0 | 30.00 | 30.00 | 30.00 | 0–60.00 | 30.00 |
| Maltose | 30.00 | 0 | 0 | 0 | 0–60.00 | 0 |
| Polyethylene glycol | 0 | 0 | 0 | 0 | 0–70.00 | 0 |
| GELRITE[c] | 1.5 | 1.5 | 2.00 | 2.00 | 0–6.00 | 0 |
| Activated Carbon | 0 | 0 | 0 | 0 | 0–0.5 | 0–0.5 |
| PLANT GROWTH REGULATORS | \multicolumn{6}{c}{Concentration (mg/L)} | | | | | |
| Auxin[d] | 1.0–3.0 | 3.0 | 1.0–3.0 | 3.0 | 3.0 | 3.0 |
| Cytokinin[e] | 0.50 | 0.50 | 0.50 | 0.50 | 0.50 | 0.50 |
| Abscisic Acid | 10.00 | 0–30.00 | 0–30.00 | 0–30.00 | 0–125.00 | 0 |

[a]Refer to Table 1 for composition of basal medium.
[b]In some Examples, defined amino acid mixtures were substituted for casein hydrolysate.
[c]GELRITE ® (gellan gum manufactured by Merck, Inc.).
[d]2,4-dichlorophenoxyacetic acid (2,4-D) or naphthalene acetic acid (NAA).
[e]$N^6$-benzylaminopurine (BAP) or $N^6$-benzyladenine (BA).
[f]For all liquid culture media used in these examples, no gelling agent was added and the medium was stored in 500 ml batches under refrigeration or frozen prior to use.

After megagametophyte explants were placed in culture, the perimeter of the dish was sealed with two wraps of NESCOFILM® sealing film (commercially available from Karlan Company). The dishes were incubated in the dark at a constant temperature of 23°±2° C. After about 7 to 21 days, embryogenic tissue extruded from the micropyle of the megagametophyte explants. At six weeks following the placement of the explant on initiation media, tissue masses that had extruded and were proliferating from individual explants were isolated to individual petri plates on maintenance medium $DCR_2$ or $WV5_2$ and assigned line numbers. After one to three months of culture on maintenance medium, the tissue cultures were cryopreserved.

Specifically, the cells were added to an equal volume of liquid DCR medium containing sorbitol, for a final concentration of 0.2–0.4M sorbitol. Erlenmeyer flasks containing the resultant suspension were incubated for 24 hours in the dark on a gyrotory shaker (commonly at 100 rpm), and then placed on ice. Aliquots of the cryoprotectant dimethyl sulfoxide (DMSO) were added to the suspension to bring final concentration of DMSO to 10%. One milliliter aliquots of the cell suspension containing DMSO were then transferred to freezing vials, placed in a programmable freezer, and cooled to −35° C. at 0.33° C. per minute. The freezing vials were subsequently immersed in liquid nitrogen inside a cryobiological storage vessel for long-term storage. Those skilled in the art of plant tissue culture will recognize that other cryopreservation protocols would be applicable to the present method.

Frozen cultures were retrieved when desired by removing individual vials from the cryobiological storage vessel and placed in 42°±2° C. water to rapidly thaw the frozen cell suspensions. The thawed cell suspensions were aseptically poured from the cryovial onto a sterile 35 μm pore size polyester membrane support placed over sterile filter paper (Whatman® no.2 filter paper, Whatman International Ltd.) for a few minutes to allow the DMSO cryoprotectant solution to diffuse away from the embryogenic tissue into the paper. The embryogenic tissue on the polyester support membrane was then transferred to $DCR_2$ maintenance medium and incubated at 23°±2° C. in the dark for 24 hours to allow additional DMSO to diffuse away from the tissue into the medium. The polyester support bearing the embryogenic tissue was then removed from the medium and transferred to fresh $DCR_2$ maintenance medium, and thereafter, every 14–21 days to a fresh plate until the amount of cells per plate reached about 1 g. The culture environment during post-cryopreservation recovery and growth was 23°±2° C. in the dark. Those skilled in the art will recognize that many different cryopreservation and recovery procedures would be suitable for use with this method and the detail in this example may not be construed to limit the application of the method.

After growth to sufficient mass on this medium as described above, the tissue cultures were placed in $DCR_4$ liquid maintenance medium (Table 2) containing activated carbon. Suspension cultures were established by inoculating a 250 ml Nephelo sidearm flask (Kontes Chemistry and Life Sciences Products) with 1 g of tissue from each of three genetically different tissue culture lines into 20 ml liquid $DCR_4$ medium. The flasks containing the cells in liquid medium were then placed on a gyrotory shaker at 100 rpm in a dark culture room at a temperature of 23°±2° C. One week later, the liquid in each flask was brought up to 35 ml by pouring 15 ml fresh medium into the culture flask and swirling to evenly distribute the cells. At 7-day intervals the cell growth was measured in the sidearm by decanting cells and medium into the sidearm portion of the flasks, allowing the cells to settle for 30 minutes and then measuring the settled cell volume (SCV). When the SCV was greater than or equal to half the maximal SCV (50% of the volume of the flask was occupied by plant cells), Suspension cultures were established as above. At 7-day intervals the cell growth was measured in the sidearm by decanting cells and medium into the sidearm portion of the flasks, allowing the cells to settle for 30 minutes and then measuring the SCV. When each suspension's SCV was greater than or equal to half the maximal SCV (50% of the volume of the flask was occupied by plant cells), it was split with half going into another sidearm 250 ml flask, and both flasks were brought up to 35 ml with fresh medium. When the SCV was greater than or equal to half the maximal SCV, each culture was transferred to a 500 ml sidearm flask containing a total of 80 ml cells and medium, for routine maintenance. The lines were maintained in culture in 500 ml sidearm flasks, splitting into additional flasks when necessary, for up to several months. All of them showed typical pine precotyledonary embryogenic cell culture morphology with long suspensor-like cells appending dense cytoplasmic head-type cells. Those skilled in the art will recognize that many different maintenance and proliferation procedures would be suitable for use with this method and the detail in this example may not be construed to limit the application of the method.

To prepare for gene transfer, a sterile fabric support (in this example PECAP® fabric support, commercially available from SEFAR Inc.) was placed in a sterile Buchner funnel and one to five milliliters of embryogenic suspension was pipetted onto the fabric support such that the embryogenic tissue was evenly distributed over the surface. The liquid medium was suctioned from the tissues using a mild vacuum. The fabric support with embryogenic tissue was removed from the Buchner funnel and placed on a GEL-RITE® gelling agent solidified $DCR_3$ preparation medium (Table 2) in 100×25 mm plastic petri dishes. Dishes were incubated in a dark growth chamber at 23°±2° C. for about 24–48 hours.

DNA was transferred into the tissues by the biolistic method described in U.S. patent application Ser. No. 09/318, 136 filed on 25 May 1999 and New Zealand Patent No. 336149, each incorporated herein by reference, using the PDS-1000/He BIOLISTICS® Particle Delivery System (available from Bio-Rad Laboratories). The DNAs of interest, here containing the visual marker gene uidA and the selection gene nptII, were precipitated onto the surface of gold microparticles, which were subsequently accelerated toward embryogenic tissue to penetrate the cell walls. Once inside the cells, DNA is released from the carrier particles and integrated randomly into the chromosomes.

The petri dishes with the fabric support and embryonic tissues were then placed into the interior of the PDS 1000/He BIOLISTICS® device and vacuum applied to a level of 28 inches Hg. The gold particles carrying the DNA were accelerated toward the embryogenic tissue following a helium build-up and bursting regulated by a 1550 psi rupture disk. In the PDS-1000/He BIOLISTICS® device the gap between the rupture disk and the macrocarrier (gap distance) was five mm and the macrocarrier travel distance was 13 mm. Following DNA transfer the petri dishes containing the fabric support and tissues were incubated in a dark growth chamber at 23°±2° C. for about 24 hours. The tissues and fabric support were transferred to semi-solid maintenance medium, $DCR_1$ (Table 2) to recover from carrier particle bombardment and incubated in a dark growth chamber at 23°±2° C. for a period of about seven days. The tissues and fabric support were transferred to a selection medium, semi-solid maintenance medium $DCR_1$ containing a level of selection agent inhibitory to the growth of non-transformed cells. In this and subsequent examples the selection agent used was GENETICIN® antibiotic at 15–30 mg/l. The plates were incubated in a dark growth chamber at 23°±2° C. for about six to twelve weeks with the fabric supports containing the tissues being transferred to the same fresh culture medium every 2–3 weeks.

Active growth on the selection medium occurred in a number of isolated sectors on some of the petri dishes. Such active growth in the presence of selection agent is an indication that the growing tissues have integrated the selection gene into their chromosomes and are stably transformed. These areas of active growth were treated as independent transformation events and are henceforth referred to as sublines. The transgenic embryogenic tissue was multiplied by transferring growing transgenic sectors to fresh semi-solid maintenance $DCR_2$ medium supplemented with selection agent, referred to hereinafter as $DCR_5$ selection medium, or semi-solid maintenance $WV5_2$ medium supplemented with selection agent, referred to hereinafter as WV5 selection medium. Dishes were incubated in a dark growth chamber at 23°±2° C. The actively growing transgenic embryogenic tissue was transferred to fresh semi-solid maintenance $DCR_5$ selection medium at 2–3 week intervals for a period of about six to twelve weeks depending on the rate of growth of the individual sublines of the transgenic embryogenic tissue.

Stable transformation was verified through a combination of growth on selection medium, assay for expression of the visual marker gene, polymerase chain reaction (PCR) amplification of specific segments of the transgene DNA sequence, and DNA blot hybridization to detect the integration of the transgenes into the genomic DNA. These techniques were carried out using techniques well known to those skilled in the art of molecular biology.

When individual transgenic sublines had reached a mass of 1 g, they were again placed into suspension culture using the methods described above. Some of the tissue was then cryopreserved using the method described above. When desired, cells from individual transgenic sublines, and previously cryopreserved cells from the corresponding non-transgenic origin lines, were retrieved from cryopreservation and cultured in suspensions again as described above. Cells from both cryopreserved and non-cryopreserved transgenic sublines were used to regenerate plants, as follows.

When the cell suspensions had been brought to approximately identical (half-maximal) SCV, equivalent amounts of suspension culture cells were pipetted onto sterile 55×55 mm square membrane supports for placement on $MSG_1$ development/maturation containing 125 mg/L ABA (Table 3 below), to assess the ability of the cultures to develop high quality harvestable cotyledonary embryos after both proliferative growth and maturation on the respective membrane treatments. Dishes were incubated in a dark growth chamber at 23°±2° C. The membrane supports were transferred to new petri dishes containing fresh medium every 3 weeks. At week 9, cotyledonary embryos were counted and those deemed suitable for germination were harvested.

TABLE 3

Composition of Development/Maturation and Germination Media Used For Pine Embryogenic Cells

| COMPONENT | Development/Maturation Medium $MSG_1$ | Pre-Germination Medium $MSG_2$ | Germination Medium $MSG_3$ |
|---|---|---|---|
| Basal medium[a] | MSG | MSG | MSG |
| | CONCENTRATION (g/L) | | |
| Ammonium Nitrate | 0 | 0 | 0.80 |
| Inositol | 0.10 | 0.10 | 0.10 |
| L-glutamine | 1.45 | 1.45 | 0 |
| Sucrose | 0 | 0 | 30.00 |
| Maltose | 60.00 | 60.00 | 0 |
| GELRITE[b] | 2.00 | 2.00 | 2.00 |
| Activated Carbon | 0–1.25 | 0 | 5.00 |
| PEG[c] | 0–100.00 | 0 | 0 |
| PLANT GROWTH REGULATORS | Concentration (mg/L) | | |
| ABA[d] | 125 | 21 | — |

[a]Refer to Table 1 for composition of basal medium.
[b]GELRITE ® (gellan gum manufactured by Merck, Inc.).
[c]Polyethylene glycol (molecular weight of 4000).
[d]Abscisic acid.

Embryos harvested from the development/maturation medium were placed over gelled medium $MSG_2$ (Table 3), in petri plates and incubated for about four weeks in the dark at a temperature of 4° C. Next, the membrane supports still bearing the embryos were placed in sealed containers at 100% relative humidity for about three weeks in the dark at a temperature of 23°±2° C. Next, the membrane supports still bearing the embryos were transferred to medium $MSG_3$ (Table 3) and incubated for about three days in the dark at a temperature of 23°±2° C. Embryos were then removed from their membrane supports and placed individually onto the surface of fresh $MSG_3$ medium in petri plates for germination in the light at a temperature of 27°±3° C. Germinating embryos were transferred to MAGENTA(g boxes containing 50–100 ml of $MSG_3$ medium for conversion to plantlets. MAGENTA® boxes containing developing plantlets were incubated in the light at 27°±3° C. for about eight to twelve weeks.

The results were that multiple transformants were obtained from each of the cell lines tested, but the number of transformants obtained from the treatment in which ABA was present during the entire period of transfer was equal to or greater than the number obtained for any other treatment for all lines tested.

Furthermore, transformants from a cell line of an elite family, progeny of the P. taeda elite line 7–56, were observed only on treatments that had contained ABA in the selection medium. In previous experiments without ABA present in the selection medium, no transformants had been detected following selection in any of twelve lines tested from the same family, or another family derived from the reciprocal cross. As shown by the present example, solely in treatments containing ABA in the selection media were we able to detect the first sublines from any line of this cross that survived selection and produced confirmed transformants.

This result demonstrated that the previous failure to detect stable transformants from this family did not result from failure to transform any cells, but from failure of these transformed pine cells to grow during selection without ABA. Stable transformants were detected after nine weeks of selection in a treatment in which 10 mg/L ABA had been added to the medium only during the first three weeks of selection, and more transformants were detected in treatments in which ABA was added to the selection medium throughout the entire nine-week selection period. This result implies that the protective effect of the ABA which allows transformed cells to survive selection is already being exerted in the initial period of selection, but that it is beneficial throughout the selection period and that without it transformants are being lost before they can be detected. This result further indicates that the improved selection method using ABA in the selection medium is enabling for the recovery of transformed cells from lines that are progeny of these elite crosses.

Plantlets with white, healthy roots and an actively growing epicotyl were transferred to a soil mix and placed under mist in a shaded greenhouse, then removed from mist, then moved to an outdoor shaded area, for acclimation before moving to full sun conditions. These treestocks were then planted on an operationally prepared site with 9 feet between rows. The trees were planted 6 feet apart along the center of the rows. Survival in the field has been approximately 93%. To our knowledge, this is the first planting worldwide containing transgenic P. taeda derived from progeny of these elite crosses.

Example 2

Use of ABA in Recovery and Selection Media for Transformed Tissue

Loblolly pine cell lines were used which had been grown and maintained as described in Example 1 above, and prepared for biolistic transformation as described in Example 1 above. In this example, only cell lines that are progeny of the elite P. taeda line 7–56 were used. Following bombardment the support membranes bearing the bombarded embryogenic cells were transferred to $DCR_2$ maintenance media, either with or without the addition of 10 mg/l ABA for one week. Following this the support membranes bearing the bombarded embryogenic cells were placed on plates containing gelled DCR selection medium with 10 mg/l abscisic acid (ABA), and cultured for three days, so that all cells were exposed to 10 mg/l ABA in the selection medium for the first three days of selection. Following this the support membranes bearing the bombarded embryogenic cells were evenly divided among gelled media containing 5, 10, or 20 mg/l ABA for a period of two weeks. Following this, the support membranes bearing the bombarded embryogenic cells were evenly divided among gelled media containing 0, 5, 10, or 20 mg/l ABA for the remaining selection period, and transferred every three weeks to fresh selection media of the same composition.

After a total often weeks of selection, the plates were examined for sublines growing in the presence of the GENETICIN® antibiotic selection agent, and cells from these sublines were observed for staining indicating the presence of the uidA transgene. The cells were also checked for the presence of sequences by PCR amplification using primers specific for both the uidA and nptII transgenes, techniques well known to those skilled in the art of plant transformation.

The results were that transformants were obtained from each of five cell lines from which transformants had never previously been recovered. Transformants were recovered only from treatments in which ABA had been added to the selection medium throughout the period of selection. Transformants were recovered from treatments in which 5, 10, or 20 mg/l had been present for the latter 9 weeks of selection, but the largest number of lines produced transformants, and the largest number of transformants were recovered from these lines, in the treatments in which ABA concentration was increased to 20 mg/l after the first transfer on selection media.

As shown by this example, we detected confirmed transformants from a desirable elite family on selection media containing as little as 5 mg/L ABA and as much as 20 mg/L ABA. A greater number of transformants was detected on treatments with increased ABA levels in the selection media.

In this example, 10 mg/L ABA in the recovery media (onto which cells are transferred following transformation, before they are subjected to selective growth or positive selection) did not significantly increase the number of transformants detected, but did not decrease it either, and may have supported the recovering health of the cells going into selection. Thus, in many of the subsequent bombardment and Agrobacterium experiments from which stable pine embryogenic transformants have been detected, we have used ABA in both the recovery and selection media.

Example 3

Use of ABA in Culture Media for Bombardment

Loblolly pine cell lines or hybrid cell lines were used which had been grown and maintained as described in Example 1 above. In this example, secondary embryogenic cultures were initiated from individual pre-stage 3 embryos. For this method to be successful, the explants or cultures must contain embryos that are pre-stage 3 in development, according to the embryo staging system of Hakman and von Arnold (1988). Pre-stage 3 embryos for use in this method could be derived from several sources, including embryogenic cultures previously initiated from immature seed explants (megagametophytes containing immature zygotic embryos), embryogenic cultures derived from immature zygotic embryo explants, embryogenic cultures grown on embryo development medium, and liquid embryogenic suspension cultures. In this example, embryogenic cultures grown for a short period on embryo development medium containing high ABA and PEG (medium $MSG_1$ of Table 3) were used, in a utility different from the usual employment of that medium to support terminal embryo development to that mature germinable embryos over a period of 8–12 weeks.

To initiate secondary embryogenic cultures from individual developing embryos, pre-stage 3 embryos with attached suspensor cells were aseptically separated from the subtending tissue using a dissecting microscope and fine-tipped forceps. The developing embryos that had been on development medium for varying lengths of time and were developed to various stages from less differentiated to translucent precotyledonary stage embryos to more opaque precotyledonary stage embryos. These isolated pre-stage 3 somatic embryos were placed on maintenance medium $DCR_2$, as listed in Table 2 except that the medium contained 10 mg/l abscisic acid. Every 14 to 21 days, vigorously proliferating secondary embryogenic tissue derived from the isolated pre-stage 3 somatic embryos was transferred to fresh medium of the same type ($DCR_1$). The amount of embryogenic tissue proliferation was quantified by measuring the size of each pre-stage 3 somatic embryo-derived mass of tissue.

It was found that tissue taken from embryo development medium at the wrong stage of development, i.e. as less differentiated callus that that bearing translucent precotyledonary stage embryos, or as embryos differentiated past the translucent precotyledonary stage, were unable to initiated secondary embryogenesis or were unable to support subsequent proliferative growth of embryogenic tissue. The ideal stage for the initiation of secondary embryogenesis followed by subsequent proliferative growth of the secondary embryogenic tissue was the same as that found necessary and sufficient for transformation in U.S. patent application Ser. No. 09/318,136 filed on 25 May 1999 and New Zealand Patent No. 336149, each incorporated herein by reference.

For transformation in this example, the tissue was bombarded using conditions described in Example 1 except that the tissue had been plated on $MSG_2$ medium containing 125 mg/L ABA and 70 g/L PEG 3–8 weeks previously, instead of on medium $DCR_3$ one day previously, so that the experimental treatment consisted of precotyledonary embryos at various stages of development. Following DNA transfer, visible pre-stage 3 embryos were dissected from the bombarded tissues and placed individually onto $DCR_2$ as described above for secondary proliferation.

Following a period of one to 14 days, when a preponderance of pre-stage 3 embryos dissected from the bombarded tissue could be seen to be beginning to proliferate secondary embryogenic cell masses, samples to be assayed for transformation were transferred to a selection medium identical to $DCR_2$ except that it contained 10 mg/l abscisic acid to initiate secondary embryogenesis. Samples of isolated pre-stage 3 embryos from each line and the secondary tissue proliferating from them were also cultured on $DCR_2$ maintenance media without selection agent to observe any effect of the bombardment treatment on proliferation. These cultures were transferred to fresh maintenance media every three weeks. Proliferation of these non-selected controls at nine weeks after dissection is recorded in Table 4.

The pre-stage 3 embryos which had been subjected to selection, and any secondary embryogenic tissue proliferating on them, were transferred every three weeks to fresh $DCR_1$ selection media. The number of stable sublines found to be actively growing on selection media at the end of the selection period is listed in Table 4. Putative transformant sublines with sufficient cell mass growing on the selective medium were further confirmed as transformed by use of polymerase chain reaction analysis and sequences from the transforming DNA, via procedures well-known to those skilled in the art.

TABLE 4

Proliferation of Secondary Embryogenic Cultures from Dissected Pre-stage 3 Embryos after Bombardment.

|  | % secondary proliferation on maintenance medium | Sublines growing on ABA selection medium, with transformation confirmed by PCR analysis |
|---|---|---|
| P. taeda, barely elongated, fine small precotyledonary | 71% | no |
| P. taeda, more elongated, still fine small precotyledonary | 69% | no |
| P. taeda, translucent precotyledonary | 91% | yes |

TABLE 4-continued

Proliferation of Secondary Embryogenic Cultures from Dissected Pre-stage 3 Embryos after Bombardment.

|  | % secondary proliferation on maintenance medium | Sublines growing on ABA selection medium, with transformation confirmed by PCR analysis |
|---|---|---|
| P. taeda x P. hybrida, translucent precotyledonary | 90% | yes |
| P. taeda, precotyledonary embryos turning opaque | 23% | none |

This example shows that the developmental stage of the starting material, controlled in $MSG_2$ by the concentration of ABA and PEG (Rutter et al. 1998 and Handley, 1999) was critical as to whether proliferating transformed sublines could be recovered. It should be noted that the stable transformants obtained here included lines from the progeny of the elite cross used in Examples 1–2.

To verify that the cultures derived from initiation of secondary somatic embryogenesis on translucent precotyledonary embryos followed by proliferative growth were indeed embryogenic and therefore could be used to regenerate pine trees, multiple secondary embryogenic cultures (sublines) initiated from pre-stage 3 somatic embryos, including a transgenic subline, were subsequently used to regenerate germinable cotyledonary somatic embryos, by the methods described in previous examples. Briefly, secondary cultures derived from individual pre-stage 3 somatic embryos were used to establish liquid suspension cultures as described in previous examples, and aliquots of these suspensions were plated on embryo development medium $MSG_2$ (Table 3) as described in previous examples. Cotyledonary somatic embryos were harvested from the embryo development medium, germinated, converted to soil, and planted in the field as described in Example 1. To our knowledge, this is the first field planting worldwide of pine plants, both non-transgenic and transgenic, derived from the secondary embryogenesis process initiated on precotyledonary pine somatic embryos.

Example4

Use of ABA in Culture Media During and After Transformation with *Agrobacterium*

This example teaches that the method also improves selection of pine embryogenic tissues that have been transformed by *Agrobacterium tumefaciens*. Those skilled in the art of plant transformation will recognize that this method improving selection may be used to select pine tissues that have been genetically modified by a variety of methods including but not limited to transformation via biolistics or *Agrobacterium*.

Seven loblolly pine cell lines or hybrid cell lines from seven widely diverse genetic backgrounds were used in this experiment. To prepare for gene transfer using *Agrobacterium*, fabric supports were sterilized by autoclaving and placed in a sterile Buchner funnel, and one to five milliliters of embryogenic suspension was pipetted onto each support such that the embryogenic tissue was evenly distributed over its surface. Following this the liquid medium was suctioned from the tissues and each support bearing the embryogenic tissue was placed on gelled medium for inoculation by *Agrobacterium*. In this case the medium used was the same as the preparation medium described in Example 1 above, except that the medium, used here for preparation and co-cultivation of the cells, contained ABA at 0, 10, or 30 mg/L as an experimental condition. Genes were then introduced into the plant material by co-cultivation with Agrobacterium(Wenck et al. 1999). Specifically, gene constructs containing a reporter gene and a selectable marker were introduced into Agrobacterium tumefaciens strain EHA105 with the virulence-enhancing plasmid pTOK47 (Wenck et al. 1999), by techniques well known to those skilled in the art, and virulence was then induced with administration of acetosyringone by commonly used techniques, well known to those skilled in the art, whereupon the induced Agrobacterium was dripped over the plant material and these were co-cultivated in the dark at 23°±2° C. for approximately 24–72 hours. Those skilled in the art recognize that many different gene constructs, plasmids, strains, media, and co-cultivation times and protocols would be suitable for use in the present method.

Following co-cultivation, cells were re-suspended into fresh $DCR_4$ liquid wash medium (Table 2) containing eradicants such as 200–400 mg/L TIMENTIN® antibiotic. The $DCR_4$ liquid wash medium was contained in sterile "baby food" jars with MAGENTA® aerated lids, conventional beakers, or multi-well plates. Resuspension was initiated by grasping the membrane support bearing the infected cells, using forceps, and rolling or folding it so that it could be taken up and placed into the liquid in the wash container. The liquid was then agitated to get the cells into suspension, and the membrane support was scraped with sterile forceps if cells appeared to be adhering to it. Once the cells were in suspension, the membrane was removed with sterile forceps.

Following this wash step, the cells were plated onto fresh sterile support membranes of the same type as used in the previous step, again by placing the fresh sterile support membranes in a sterile Buchner funnel, pipetting the suspension of plant cells onto the membranes, and again suctioning the liquid medium from the tissues using a mild vacuum. The cells were again resuspended in and cultured in fresh sterile wash medium by agitating the membrane bearing the cells in the liquid, again removing cells that appeared to be adhering by gently scraping with forceps. The cells were then re-plated on fresh membrane supports over Buchner funnels. This procedure was repeated twice before the cells were again plated on supports as described above.

Supports bearing approximately 0.1 g of embryogenic tissue were divided onto recovery media (having the same formulation as the maintenance medium except for the addition of 400 mg/L TIMENTIN® antibiotic) either containing or lacking ABA. Following a one-week recovery period during which the cells were observed for resurgence of Agrobacterium, the polyester support membranes bearing the pine somatic embryogenic tissue were divided onto DCR selection media either containing or lacking ABA. Concentrations of ABA used in all these media were 0, 10, and 30 mg/l.

Cells were maintained on the selection media, with transfer of the polyester support membranes to fresh selection media of the same composition, every two weeks for a total of eight weeks of selection. Cells from actively growing sublines from selection were examined using stereomicroscopes for the expression of the visual marker gene uidA at the conclusion of the selection period. All of the sublines capable of active growth on selection medium were seen to express levels of the visual marker gene product that enabled them to be readily distinguished from non-selected cells. This continuing expression of the transgenes after at least twelve weeks following bombardment confirmed the integration of the transgenes in these sublines. Such integration, and the absence of undetected contaminating Agrobacterium,was further confirmed by PCR amplification using primers designed to amplify sequences from an endogenous control and the uidA, nptII, and virD genes, by techniques well known to those skilled in the art of plant transformation. The results are presented in Table 5 below.

TABLE 5

Effect of ABA Concentration on Average (n = 12) Number of Transformants observed per Selection Plate Bearing 0.1 g Agrobacterium-inoculated Pine Cells at Start of Recovery

| Concentration of ABA (mg/l) in | | | P. taeda (P) or P. rigida Hybrid (H)Embryogenic Cell Line | | | | | | |
|---|---|---|---|---|---|---|---|---|---|
| preparation medium | recovery medium | selection medium | H1 | P1 | P2 | P3 | P4 | P5 | P6 |
| 0 | 0 | 0 | 9.6 +/− 4.8 | 0.0 +/− 0.0 | 1.3 +/− 1.9 | 20.3 +/− 2.2 | 33.4 +/− 13.5 | 0.4 +/− 0.9 | 1.3 +/− 1.2 |
| 0 | 0 | 30 | 21.1 +/− 6.5 | 0.0 +/− 0.0 | 8.8 +/− 4.8 | 22.3 +/− 5.4 | 34.9 +/− 9.7 | 5.5 +/− 3.1 | 3.3 +/− 2.8 |
| 0 | 10 | 10 | 19.0 +/− 6.5 | 0.0 +/− 0.0 | 1.0 +/− 1.0 | 23.3 +/− 2.8 | 28.8 +/− 11.6 | 2.4 +/− 2.0 | 3.2 +/− 1.4 |
| 0 | 10 | 30 | 21.6 +/− 8.6 | 0.1 +/− 0.3 | 0.3 +/− 0.5 | 26.0 +/− 6.9 | 30.9 +/− 9.3 | 7.2 +/− 2.1 | 3.2 +/− 1.5 |
| 0 | 30 | 30 | 15.1 +/− 4.9 | 0.8 +/− 0.6 | 5.2 +/− 6.1 | 18.6 +/− 5.1 | 28.6 +/− 7.6 | 3.3 +/− 2.1 | 2.3 +/− 2.6 |
| 10 | 10 | 10 | | | 10.0 +/− 3.7 | | | | |
| | | | 21.9 +/− 8.4 | 1.3 +/− 0.9 | | 22.6 +/− 4.3 | 27.8 +/− 9.0 | 10.3 +/− 2.4 | 4.5 +/− 1.3 |
| 30 | 30 | 30 | 21.8 +/− 9.9 | 0.4 +/− 0.8 | 5.3 +/− 2.5 | 21.1 +/− 2.3 | 27.3 +/− 7.4 | 14.3 +/− 3.5 | 2.3 +/− 1.1 |
| 30 | 10 | 10 | 22.9 +/− 10.1 | 0.3 +/− 0.5 | 5.9 +/− 2.4 | 21.6 +/− 3.6 | 22.7 +/− 7.0 | 11.3 +/− 2.4 | 3.1 +/− 2.3 |
| 0 | 0 | 10 | 27.0 +/− 11.2 | 0.3 +/− 0.9 | 5.8 +/− 2.3 | 21.7 +/− 3.6 | 27.5 +/− 11.4 | 18.1 +/− 4.0 | 3.9 +/− 1.5 |

Cell lines used in this experiment varied from highly transformable to never previously transformed, in order to see the effect of ABA on a variety of types. Some of the lines were from the elite cross used in Examples 1–2, and some were from other elite crosses whose progeny had never previously been transformed. As can be seen in the table above, 10 or 30 mg/l ABA concentration in the preparation medium was neutral or beneficial to the observation of transformants. ABA in the recovery medium was similarly neutral or beneficial, except that it was required in both the recovery and selection medium in order to observe transformants in one line. ABA in the selection medium is clearly beneficial for several of the Also seen in this example, pine somatic embryogenic masses of all lines cultured in the presence of either 10 or 30 mg/L ABA during and after co-cultivation with *Agrobacterium* showed fewer necrotic foci (these appeared upon microscopic examination to be derived from the death of precociously developing embryos in the cultures) than did pine somatic embryogenic masses which were cultured during and after co-cultivation on media that did not contain ABA.

In this example, transformants were obtained from all lines, including lines from two families that had never previously been transformed. In subsequent experiments using *Agrobacterium* transformation and the methods of this Example, transformants have been recovered in lines from every one of 14 families attempted, in an average of 71% of the lines attempted from any given family.

Multiple separate transformants of three *P. taeda* lines and a hybrid line generated in this example were cryopreserved and then retrieved, simultaneously with cells of the respective non-transformed origin lines retrieved from cryopreservation by the same operators and method, for testing of the effects of the transformation and selection processes on their embryogenicity. Those skilled in the art will recognize that this illustrates that the methods used are applicable to recovering regenerable transformants from cell lines with a variety of histories and using a variety of methods and plasmids for transformation. Hundreds of embryos have now been developed, matured, and germinated from *Agrobacterium* transformants of both *P. taeda* and hybrid lines selected using the methods in this example. Using the methods described in Example 1, these embryos have been converted to treestocks suitable for field planting. Stable transformation of these lines has been verified by continues expression of the uidA gene in woody and needle tissue, and by Southern blotting of genomic DNA isolated from needles of regenerated treestocks, using the uidA coding region as a probe.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

Bibliography

Becwar, M. R. et al. (1990). Initiation Of Embryogenic Cultures And Somatic Embryo Development In Loblolly Pine (*Pinus Taeda*). *Canadian Journal of Forest Research* 20:810–817.

Becwar, M. R. et al. (1995). Method for regeneration of coniferous plants by somatic embryogenesis. U.S. Pat. No. 5,413,930.

Becwar, M. R. et al. (1996). Method for regeneration of coniferous plants by somatic embryogenesis. U.S. Pat. No. 5,506,136.

Cello, L. M. and Olsen, W. L. (1984). Method for transforming plant cells. U.S. Pat. No. 4,459,355.

Coke, J. E. (1996). Basal nutrient medium for in vitro cultures of loblolly pine. U.S. Pat. No. 5,534,433.

Gupta, P. K. and Durzan, D. J. (1985). Shoot multiplication from mature trees of Douglas-fir (*Pseudotsuga menziesii*) and sugar pine (*Pinus lambertiana*). *Plant Cell Reports* 4:177–179.

Gupta, P. K. and G. S. Pullman. Method for reproducing coniferous plants by somatic embryogenesis using abscisic acid and osmotic potential variation. U.S. Pat. No. 5,036,007—issued Jul. 30, 1991.

Hakman, I. and S. von Arnold. 1988. Somatic embryogenesis and plant regeneration from suspension cultures of *Picea glauca* (White spruce). Physiologia Plantarum 72:579–587.

Handley, L. W. III. (1999). Method for regeneration of coniferous plants by somatic embryogenesis in culture media containing abscisic acid. U.S. Pat. No. 5,856,191.

Handley, L. W. III and Godbey, A. P. (1996). Embryogenic Coniferous Liquid Suspension Cultures. U.S. Pat No. 5,491,090.

Klimaszewska, K., Sutton, B. C. S., Polonenko, D. R., Cyr, D. R., Stodola, T. F. (2001) Maturation of somatic embryos. U.S. Pat. No. 6,200,809.

Rutter, M. R., Handley, L. W., Becwar; M. R. (1998) Method for regeneration of coniferous plants by somatic embryogenesis employing polyethylene glycol. U.S. Pat. No. 5,731,191

Sederoff, R. R. et al. (1988). Method for transforming Pine. U.S. Pat. No. 4,886,937.

Smith, D. R. (1996). Growth Medium. U.S. Pat. No. 5,565,355.

von Arnold and Hakman (1988). Regulation of somatic embryo development in *Picea abies* by abscisic acid (ABA). *Journal of Plant Physiology* 132:164–169.

Walter, C., D. R. Smith, M. B. Connett, L. Grace and D. W. R. White. 1994. A Biolistic approach for the transfer and expression of a gusA reporter gene in embryogenic cultures of *Pinus radiata*. Plant Cell Reports 14:69–74.

Walter, C., and D. R. Smith. 1997. Stable transformation of Undifferentiated Conifer Cells. WO 97/01641. Filed Jun. 25, 1996. Published Jan. 16, 1997.

Wenck, A. R. et al. (1999). High efficiency *Agrobacterium*-mediated transformation of Norway spruce and loblolly pine. *Plant Molecular Biology* 39:407–416.

What is claimed is:

1. A method for regenerating genetically modified plants of pine of the genus *Pinus* subgenus *Pinus* selected from the group consisting of Southern yellow pines and hybrids between Southern yellow pines, which comprises selecting transgenic embryogenic pine cells using a selection medium comprising a selection agent and an agent that regulates differentiation of embryos from embryogenic cells, said differentiation agent is abscisic acid (ABA), and regenerating genetically modified plants from said selected transgenic embryogenic pine cells.

2. The method of claim 1, wherein said Southern yellow pines are selected from the group consisting of *Pinus taeda, Pinus elliotii,* and *Pinus caribaea.*

3. The method of claim 1, wherein the transgenic embryogenic pine cells are prepared by transforming pine cells of said pine using a transformation medium comprising ABA.

4. The method of claim 3, which further comprises culturing the transgenic embryogenic pine cells using a recovery medium comprising ABA prior to selection.

5. The method of claim 3, wherein said Southern yellow pines are selected from the group consisting of *Pinus taeda, Pinus elliotii,* and *Pinus caribaea.*

6. The method of claim 1, wherein said selection medium is a gel medium.

7. The method of claim 1, wherein said selection medium is a layer and said cells are cultured on a support membrane placed over said layer which is placed on a gel medium.

8. The method of claim 7, wherein said layer is a liquid medium.

9. The method of claim 7, wherein said layer is a filter paper with a liquid medium absorbed therein.

10. The method of claim 7, wherein said support membrane is prepared from a material selected from the group consisting of polyester, polypropylene and a liquid permeable fluoropolymer fabric.

11. The method of claim 3, wherein said selection medium is a gel medium.

12. The method of claim 3, wherein said selection medium is a layer and said cells are cultured on a support membrane placed over said layer which is placed on a gel medium.

13. The method of claim 12, wherein said layer is a liquid medium.

14. The method of claim 12, wherein said layer is a filter paper with a liquid medium absorbed therein.

15. The method of claim 12, wherein said support membrane is prepared from a material selected from the group consisting of polyester, polypropylene and a liquid permeable fluoropolymer fabric.

16. The method of claim 3, wherein said transformation is transformation by *Agrobacterium*.

17. The method of claim 16 which further includes the eradication of *Agrobacterium* from pine cells subjected to *Agrobacterium* transformation following transformation.

18. The method of claim 17, wherein the eradication is performed using on medium comprising ABA.

19. The method of claim 3, wherein said transformation is transformation by particle bombardment.

* * * * *